(12) United States Patent
Bearinger et al.

(10) Patent No.: US 8,882,786 B2
(45) Date of Patent: Nov. 11, 2014

(54) SYSTEM FOR CLOSURE OF A PHYSICAL ANOMALY

(75) Inventors: Jane P. Bearinger, Livermore, CA (US); Duncan J. Maitland, Pleasant Hill, CA (US); Daniel L. Schumann, Concord, CA (US); Thomas S. Wilson, Castro Valley, CA (US)

(73) Assignee: Lawrence Livermore National Security, LLC., Livermore, CA (US)

( * ) Notice: Subject to any disclaimer, the term of this patent is extended or adjusted under 35 U.S.C. 154(b) by 1691 days.

(21) Appl. No.: 10/781,582

(22) Filed: Feb. 17, 2004

(65) Prior Publication Data

US 2005/0182428 A1    Aug. 18, 2005

(51) Int. Cl.
*A61B 17/08* (2006.01)
*A61B 17/00* (2006.01)

(52) U.S. Cl.
CPC ... *A61B 17/0057* (2013.01); *A61B 2017/00637* (2013.01); *A61B 2017/00867* (2013.01); *A61B 2017/00654* (2013.01); *A61B 2017/00672* (2013.01)
USPC ........................................................ 606/151

(58) Field of Classification Search
USPC ......... 606/151, 139, 108, 219, 143, 144, 148, 606/213–216, 228, 232; 623/23.72
See application file for complete search history.

(56) References Cited

U.S. PATENT DOCUMENTS

| | | | |
|---|---|---|---|
| 3,604,425 A | 9/1971 | Le Roy | |
| 3,757,629 A | 9/1973 | Schneider | |
| 3,805,337 A | 4/1974 | Branstetter | |
| 4,192,315 A | 3/1980 | Hilzinger et al. | |
| 4,217,902 A | 8/1980 | March | |
| 4,396,139 A | 8/1983 | Hall et al. | |
| 4,485,816 A | 12/1984 | Krumme | |
| 4,586,503 A | 5/1986 | Kirsch et al. | |
| 4,777,950 A | 10/1988 | Kees, Jr. | |
| 4,860,746 A | 8/1989 | Yoon | |
| 4,917,087 A | 4/1990 | Walsh et al. | |
| 5,007,921 A | 4/1991 | Brown | |
| 5,026,390 A | 6/1991 | Brown | |
| 5,049,591 A * | 9/1991 | Hayashi et al. | 521/159 |
| 5,053,008 A | 10/1991 | Bajaj | |
| 5,061,274 A | 10/1991 | Kensey | |

(Continued)

FOREIGN PATENT DOCUMENTS

| EP | 0 337 918 B1 | 9/1994 |
|---|---|---|
| WO | WO 97/20505 | 6/1997 |
| WO | WO 98/24374 | 6/1998 |

OTHER PUBLICATIONS

Adams, H.P., Jr., et al., "Guidelines for the Management of Patients with Acute Ischemic Stroke: A Statement for Healthcare Professionals from a Special Writing of the Group of the Stroke Council," American Heart Association, Stroke, 25, 1994, 27 pages.

(Continued)

*Primary Examiner* — Gregory Anderson
(74) *Attorney, Agent, or Firm* — Eddie E. Scott

(57) ABSTRACT

Systems for closure of a physical anomaly. Closure is accomplished by a closure body with an exterior surface. The exterior surface contacts the opening of the anomaly and closes the anomaly. The closure body has a primary shape for closing the anomaly and a secondary shape for being positioned in the physical anomaly. The closure body preferably comprises a shape memory polymer.

19 Claims, 7 Drawing Sheets

(56) References Cited

U.S. PATENT DOCUMENTS

| | | | |
|---|---|---|---|
| 5,156,609 | A | 10/1992 | Nakao et al. |
| 5,176,648 | A | 1/1993 | Holmes et al. |
| 5,192,301 | A * | 3/1993 | Kamiya et al. ............... 606/213 |
| 5,192,302 | A | 3/1993 | Kensey et al. |
| 5,222,974 | A | 6/1993 | Kensey et al. |
| 5,304,184 | A | 4/1994 | Hathaway et al. |
| 5,366,458 | A | 11/1994 | Korthoff et al. |
| 5,478,354 | A | 12/1995 | Tovey et al. |
| 5,527,322 | A | 6/1996 | Klein et al. |
| 5,549,633 | A * | 8/1996 | Evans et al. ................. 606/139 |
| 5,571,181 | A * | 11/1996 | Li ............................. 623/23.75 |
| 5,634,936 | A * | 6/1997 | Linden et al. ................ 606/213 |
| 5,674,231 | A | 10/1997 | Green et al. |
| 5,683,405 | A | 11/1997 | Yacoubian et al. |
| 5,695,505 | A | 12/1997 | Yoon |
| 5,782,844 | A | 7/1998 | Yoon et al. |
| 5,782,861 | A | 7/1998 | Cragg et al. |
| 5,810,846 | A | 9/1998 | Virnich et al. |
| 5,810,851 | A | 9/1998 | Yoon |
| 5,830,125 | A | 11/1998 | Scribner et al. |
| 5,836,306 | A * | 11/1998 | Duane et al. ................. 600/585 |
| 5,910,155 | A | 6/1999 | Ratcliff et al. |
| 5,910,357 | A | 6/1999 | Hachisuka et al. |
| 5,964,744 | A | 10/1999 | Balbierz et al. |
| 6,034,149 | A * | 3/2000 | Bleys et al. ................... 521/155 |
| 6,059,815 | A | 5/2000 | Lee et al. |
| 6,086,599 | A | 7/2000 | Lee et al. |
| 6,090,072 | A | 7/2000 | Kratoska et al. |
| 6,102,917 | A | 8/2000 | Maitland et al. |
| 6,102,933 | A | 8/2000 | Lee et al. |
| 6,120,515 | A | 9/2000 | Rogers et al. |
| 6,160,084 | A | 12/2000 | Langer et al. |
| 6,174,322 | B1 | 1/2001 | Schneidt |
| 6,388,043 | B1 * | 5/2002 | Langer et al. ................. 528/80 |
| 6,391,048 | B1 | 5/2002 | Ginn et al. |
| 6,471,715 | B1 | 10/2002 | Weiss |
| 2002/0133193 | A1 | 9/2002 | Ginn et al. |
| 2003/0009180 | A1 | 1/2003 | Hinchliffe et al. |
| 2003/0144695 | A1 | 7/2003 | McGuckin, Jr. et al. |
| 2006/0155330 | A1 * | 7/2006 | Michlitsch ................... 606/232 |

OTHER PUBLICATIONS

Li, Y., et al., "Multiphase Structure of a Segmented Polyurethane: Effects of Temperature and Annealing," Macromolecules, 25, 1992, pp. 7365-7372.

Wheatcraft, D., "On the Offensive Against Brain Attack," Science and Technology Review, Jun. 1997; 10 pages.

Lambda, N.M.K., et al., Polyurethanes in Biomedical Applications, CRC Press, New York, 1998, 30 pages.

Kim, B.Y., et al., "Polyurethane Ionomers Having Shape Memory Effects," Polymer, 39(13), 1998, pp. 2803-2808.

Kim, B.K, et al., "Polyurethanes Having Shape Memory Effects," Polymer, 37(26), 1996, pp. 5781-5793.

Hayashi, S., "Properties and Applications of Polyurethane-Series Shape Memory Polymer," Proceedings from the Annual Technical Conference (ANTEC) of the Society of Plastics Engineers, 1994, pp. 1998-1999.

Wang, M., et al., "Recovery as a Measure of Oriented Crystalline Structure in Poly(ether ester)s Based on Poly(ethylene oxide) and Poly(ethylene terephthalate) Used as Shape Memory Polymers," J. Pol. Sci. Pol. Phys.; 37, 1999, pp. 101-112.

Li, F., et al., "Shape Memory Effect of Ethylene-Vinyl Acetate Copolymers," J. Appl. Pol. Sci., 71, 1999, pp. 1063-1070.

Irie, J., et al., "Shape Memory Polymers," chapter 9 of Shape Memory Materials, Cambridge University Press, Cambridge, 1998, pp. 203-219.

Takahashi, T., et al., "Structure and Properties of Shape-Memory Polyurethane Block Copolymers," J. Appl. Pol. Sci., 60, 1996, p. 1061.

Li, F., et at., Studies on Thermally Stimulated Shape Memory Effect of Segmented Polyurethanes,: J. Appl. Pol. Sci., 1997, pp. 1511-1516.

Lin, J. R., et al., Study on Shape-Memory Behavior of Polyether-Based Polyurethanes. I. Influence of Hard-Segment Content., J. Appl. Pol. Sci., 69, 1998, pp. 1563-1574.

Lin, J. R., et al., Study on Shape-Memory Behavior of Polyether-based Polyurethanes. II. Influence of Soft-Segment Molecular Weight., J. Appl. Pol. Sci., 69, 1998, pp. 1575-1586.

Lou, X., et al., "Thermally Stimulated Shape Memory Behavior of Ethylene Oxide-Ethylene Terephthalate Segmented Copolymer," J. Appl. Pol. Sci., 1997, pp. 2433-2440.

Kindler, D.D., et al., "Update on Therapies for Acute Ischemic Stroke," Neurosurg. Focus 8(5), 2000, p. 1-5.

* cited by examiner

SYSTEM FOR CLOSURE OF A PHYSICAL ANOMALY

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to closure systems and more particularly to apparatus and methods for closure of a physical anomaly.

2. State of Technology

U.S. Patent Application 2003/0144695 by James F. McGuckin and Richard T. Briganti, published Jul. 31, 2003, and U.S. Patent Application 2003/0009180 by Peter W. J. Hinchliffe, James F. McGuckin, Richard T. Briganti, and Walter H. Peters, published Jan. 9, 2003, for a vascular hole closure device provides the following state of the technology information, "During certain types of vascular surgery, catheters are inserted through an incision in the skin and underlying tissue to access the femoral artery in the patient's leg. The catheter is then inserted through the access opening made in the wall of the femoral artery and guided through the artery to the desired site to perform surgical procedures such as angioplasty or plaque removal. After the surgical procedure is completed and the catheter is removed from the patient, the access hole must be closed. This is quite difficult not only because of the high blood flow from the artery, but also because there are many layers of tissue that must be penetrated to reach the femoral artery."

U.S. Patent Application 2002/0133193 published Sep. 19, 2002, and U.S. Pat. No. 6,391,048 issued May 21, 2002, to Richard S. Ginn and W. Martin Belef, for an integrated vascular device with puncture site closure component and sealant and methods of use provides the following state of the technology information, "Catheterization and interventional procedures, such as angioplasty and stenting, generally are performed by inserting a hollow needle through a patient's skin and muscle tissue into the vascular system. A guide wire then is passed through the needle lumen into the patient's blood vessel. The needle is removed and an introducer sheath is advanced over the guide wire into the vessel. A catheter typically is passed through the lumen of the introducer sheath and advanced over the guide wire into position for a medical procedure. The introducer sheath therefore facilitates insertion of various devices into the vessel while minimizing trauma to the vessel wall and minimizing blood loss during a procedure. Upon completion of the medical procedure, the catheter and introducer sheath are removed, leaving a puncture site in the vessel. Commonly, external pressure is applied until clotting and wound sealing occurs. However, this procedure is time consuming and expensive, requiring as much as an hour of a physician's or nurse's time, is uncomfortable for the patient, and requires that the patient be immobilized in the operating room, cathlab, or holding area. Furthermore, a risk of hematoma exists from bleeding prior to hemostasis."

U.S. Pat. No. 6,174,322 issued Jan. 16, 2001 to Bernhard Schneidt for an Occlusion device for the closure of a physical anomaly such as a vascular aperture or an aperture in a septum provides the following state of the technology information, "The human circulatory system is comprised of a cardiovascular circulation and pulmonary circulation. In the embryonic phase of the development of a human being, the two circulatory systems are joined by the ductus arteriosus. The ductus connects the aorta (systemic circulation) with the pulmonary artery (pulmonary circulation). In the normal development of an infant, this ductus closes after birth. In pathological development, the ductus may not close so that the two circulatory systems remain connected even after birth. This can reduce the life expectancy of the infant. Closure of the ductus by means of a surgical procedure is well-known. However, this procedure is very cost-intensive and is connected with a risk for the patient. Closure of the ductus by means of an IVALON® (polyvinyl alcohol) foam plug (Porstmann method) is also well-known. In this case, a guide rail is introduced via a femoral vein into the aorta, through the ductus into the pulmonary artery and from there through the right ventricle and the right atrium and finally to the outside again via the opposite femoral vein. The ductus plug is then pushed into the ductus where it is "jammed in place." Owing to the high pressure differential between the aorta and pulmonary artery, high demands are placed on the fixation of the ductus plug within the ductus."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides apparatus and methods for closure of a physical anomaly. The closure is provided by a closure body with an exterior surface. The exterior surface contacts the opening of the anomaly and closes the anomaly.

The closure body has a secondary shape that allows closure body to be positioned in the physical anomaly. The closure body is positioned in the passage of the physical anomaly. The closure body is activated causing the closure body to change to its primary shape and close the anomaly. The primary shape allows the closure body's exterior surface to contact the inner surface of the passage of the anomaly and closes the anomaly.

In one embodiment, the present invention provides an apparatus for closure of a physical anomaly having a passage with the passage having an inner surface extending around the passage. A polymer body, such as a shape memory polymer (SMP), has an exterior surface and the exterior surface of the polymer body contacts the inner surface of the physical anomaly extending around the passage and closing the passage of the physical anomaly. The polymer body has a primary shape for closing the anomaly and a secondary shape for being positioned in the physical anomaly.

In one embodiment, the present invention provides a method for the closure of a physical anomaly wherein the physical anomaly has a passage. A closure body is provided. The closure body has a secondary shape for being positioned in the passage of the physical anomaly and a larger primary shape for closing the anomaly. The closure body is positioned in the passage of the physical anomaly when the closure body is in the secondary shape. The closure body is activated to change to the closure body to its larger primary shape for closing the anomaly.

Uses of the present invention comprise systems for the closure of physical anomalies in general. Embodiments of the present invention are used for the closure of punctures in vascular or non-vascular walls in the body. For example, arteriotomy puncture sites result from minimally invasive catheter-based procedures. Embodiments of the present invention are used for closure of punctures in vascular or non-vascular walls in the body. Embodiments may also be used for closure of septal defects and/or ductus.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
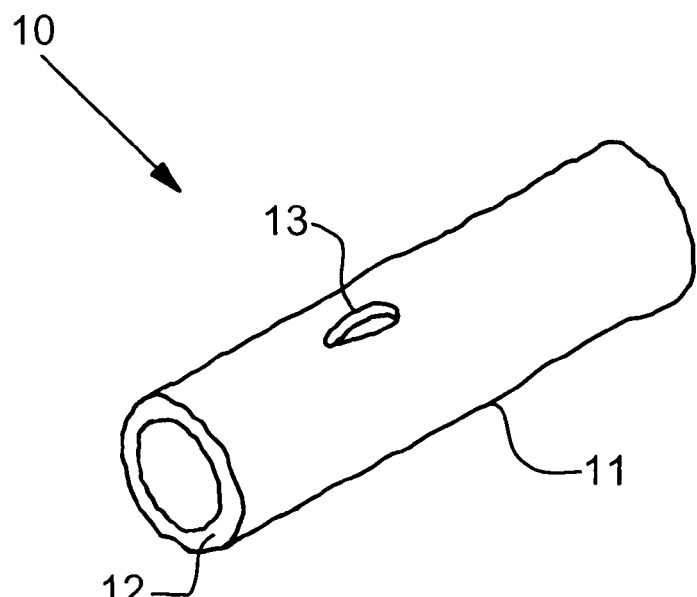
FIG. 1 is an isometric schematic of a puncture site through a vessel wall.

Referring now to the drawings, to the following detailed description, and to incorporated materials, detailed information about the invention is provided including the description of specific embodiments.

Numerous prior art devices have been developed for percutaneously sealing a vascular puncture by occluding or suturing the puncture site. For example, U.S. Pat. Nos. 5,192,302 and 5,222,974 (Kensey et al.) describe the use of a biodegradable plug delivered through the introducer sheath into the puncture site. When deployed, the plug seals the vessel and provides hemostasis. Such devices have been slow to gain acceptance in the medical community, however, due to difficulties encountered in positioning the plug within the vessel. Additionally, the agents used to occlude the puncture site are animal-derived, typically collagen-based and sometimes elicit a secondary healing or immuno-response. Another prior art technique involves percutaneously suturing the puncture site with specialized apparatus. Such apparatus is described, for example, in U.S. Pat. No. 5,304,184 (Hathaway et al.). Percutaneous suturing devices can be effective, but the reliability of the knot tying procedure is questionable and a significant degree of skill may be required on the part of the practitioner. Also, subcutaneous oozing has been reported.

In view of the above, there is a need to provide apparatus and methods suitable for vascular puncture closure that overcome the disadvantages of previously known devices, including high cost, complications, infection, blood flow restrictions, device embolization, poor apposition, and vascular obstruction with ischemia. There is also a need to provide apparatus and methods for vascular puncture closure that quickly, easily, and effectively achieve hemostasis and allow for re-intervention. There is also a need to provide apparatus and methods suitable for vascular puncture closure that do not introduce animal-derived material into the bloodstream. Procedures are using smaller sheaths and there is a need to leave materials related to the closure device in the body permanently. It is desirable to only include a small amount of material to quickly help seal off the vessel, but then allow for biological healing, resorption of material placed in the vessel and ability to reintervene in same location if necessary.

The present invention provides apparatus and methods for closure of a physical anomaly. The closure is provided by a polymer body with an exterior surface. The exterior surface contacts the opening of the anomaly and closes the anomaly. The polymer body has a primary shape for closing the anomaly and a secondary shape that allows it to be positioned in the physical anomaly. The detailed description of the apparatus and methods for closure of a physical anomaly serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Uses of the present invention comprise systems for the closure of physical anomalies in general. Embodiments of the present invention are used for the closure of punctures in vascular or non-vascular walls in the body, including septal defects and patent ductus. For example, arteriotomy puncture sites result from minimally invasive catheter-based procedures. Closure of arteriotomy puncture sites illustrate the present invention's potential for improving the outcome for catheter lab patients. Since the introduction of vascular closure devices, the worldwide market has grown to approximately $290 million. Over 7.5 million catheterization procedures are performed annually and approximately 30 percent of these currently use closure devices. Clearly, the potential benefit to the patient and the opportunity for future growth is significant.

Referring now to FIG. 1, the first of a series of figures will describe an embodiment of the present invention that provides a closure system for procedures such as arteriotomies. FIG. 1 is an isometric schematic of a puncture site 13 through the vessel wall 12 of a vessel 11. The puncture is created with a needle to allow for cathlab procedures and results in a defect in the vessel wall that requires repair. The schematic of FIG. 1 is designated generally by the reference numeral 10.

These embodiments of the present invention provide methods and apparatus for sealing arterial wounds with a closure body. In some of the embodiments, the closure body is fabricated from a "shape memory polymer" (SMP), which can be formed into a specific "primary" shape, compressed into a "secondary" stable shape, then controllably actuated so that it recovers its primary shape. The closure body in a preferred embodiment is biodegradable.

In order to close such sites, a closure body, in one embodiment a polymeric foam, is advanced to the puncture site in order to seal the site. The foam is disposed at the end of a plunger or restraint tube in some of the embodiments. In one embodiment, the foam is compacted around the base of a plunger. Alternatively, a portion of the distal end of a restraint tube is pulled back to actuate or deploy the foam into the desired location and into its expanded shape. The polymer adheres to the walls of the artery and has enough integrity to close off the vessel and prevent leakage. All catheters and tubing are then withdrawn.

Interventional procedures using catheters, such as angioplasty and stenting, are typically performed by inserting a hollow needle through a patient's skin and muscle tissue into the vascular system. Next, a guide wire is passed through the needle lumen into the patient's blood vessel. The needle is removed and an introducer sheath is advanced over the guide wire into the vessel. A catheter typically is passed through the lumen of the introducer sheath and advanced over the guide wire into position for a medical procedure. The introducer sheath enables insertion of various devices into the vessel, minimizes trauma to the vessel wall and minimizes blood loss during a procedure.

Upon completion of the medical procedure, the catheter and introducer sheath are removed, leaving a puncture site in the vasculature. Manual, external pressure may be applied to close vessel walls until clotting and wound sealing occurs. This procedure is time consuming and expensive, requiring as much as an hour of a health care professional's time, causing discomfort for the patient, and requiring patient immobilization. The patient is restricted to bed rest and monitored for up to 24 hours. Some procedures result in hematomas from bleeding prior to hemostasis.

Figure 2:
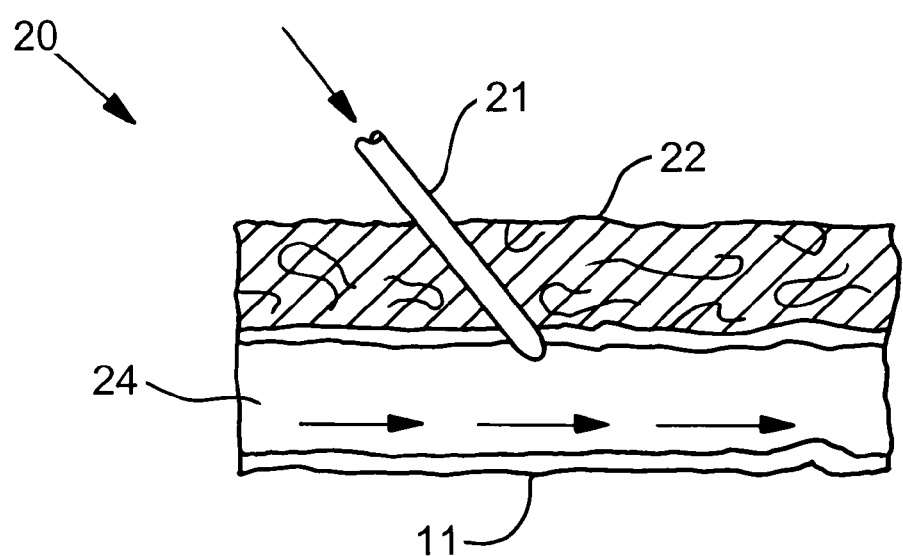
FIG. 2 is side section of a puncture tract through a vessel.

FIG. 2 is the second of the series of figures that describe an embodiment of the present invention that provides a closure system for procedures such as arteriotomies. FIG. 2 is side section of the puncture tract 21 through the wall of the vessel 11. The puncture is created with a needle to allow for cathlab procedures and results in a defect in the vessel wall that requires repair. The puncture tract 21 extends through the epidermis, dermis, fat 22 into the region of blood flow 24. The illustration of FIG. 2 is designated generally by the reference numeral 20.

Figure 3:
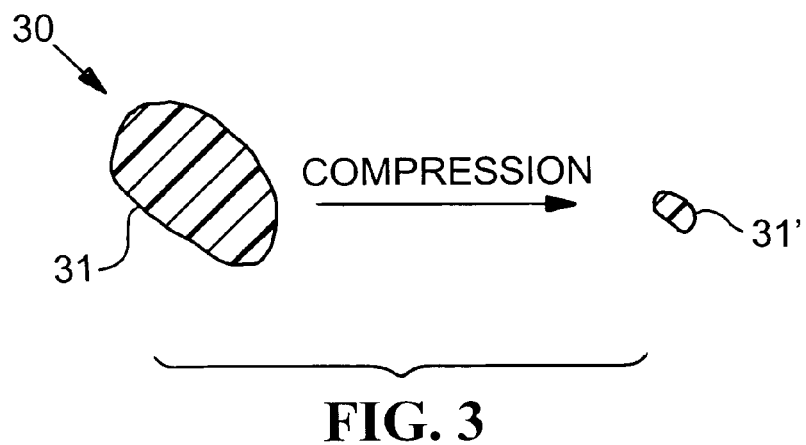
FIG. 3 is a schematic of a closure body in its expanded state and the closure body in its compressed state.

FIG. 3 is the third of the series of figures that describe an embodiment of the present invention that provides a closure system for procedures such as arteriotomies. FIG. 3 is a schematic of a closure body 31 in its expanded state and the closure body 31' in its compressed state. The closure body 31' is compressed to a smaller volume before deployment. The illustration of FIG. 3 is designated generally by the reference numeral 30. The closure body 31 and 31' is made of a shape memory material.

Shape-memory materials have the useful ability of being formable into a primary shape, being reformable into a stable secondary shape, and then being controllably actuated to recover their primary shape. Both metal alloys and polymeric materials can have shape memory. In the case of metals, the shape-memory effect arises from thermally or stress induced solid phase transformations in which the lattice structure of the atoms changes, resulting in macroscopic changes in modulus and dimensions. In the case of polymeric materials, the primary shape is obtained after processing and fixed by physical structures or chemical crosslinking. The secondary shape is obtained by deforming the material while in an elastomeric state, and that shape is fixed in one of several ways including cooling the polymer below a crystalline, liquid crystalline, or glass transition temperature; by inducing additional covalent or ionic crosslinking, etc. While in the secondary shape some or all of the polymer chains are perturbed from their equilibrium random walk conformation, having a certain degree of bulk orientation. The oriented chains have a certain potential energy, due to their decreased entropy, which provides a driving force for shape recovery. However, they do not spontaneously recover, due to either kinetic (if below their lower Tg) or physical restraints (physical or chemical crosslinks). Recovery to the primary shape is achieved by removing restraint or stress induced compression, e.g., heating the polymer above its glass transition or melting temperature, removing ionic or covalent crosslinks, etc. Both shape memory alloys (SMAs) and SMPs are used for the closure body 31 and 31' in embodiments of the present invention.

In the embodiment shown in FIG. 3, the closure device illustratively is fabricated from a "shape memory polymer" (SMP), forming the SMP closure body 31 which can be formed into a specific "primary" shape, compressed into a "secondary" stable shape as illustrated by the SMP closure body 31', then controllably actuated so that it recovers its primary shape illustrated by the SMP closure body 31. The SMP closure body 31 and 31' in a preferred embodiment is biodegradable.

The polymer is an SMP, i.e., a polymer which can be formed into a primary or equilibrium shape, re-formed into a stable secondary or stressed shape, and actuated by various means to recover its primary shape. The deployed polymer takes up a larger volume while maintaining a similar shape or alternatively assuming a specified deployed shape to the constrained material. In one embodiment, the polymer is deployed into a "barbell" shape to anchor the polymer in place effectively. In another embodiment, the polymer is "band" shaped and covers the entire outer circumference of the vessel wall, via a pull-tie type apparatus or a bent band that conforms to the vessel wall post actuation. In another embodiment the polymer is a foam and may also be biodegradable. In one embodiment, the method of actuation is via imparted physical stress. In other embodiments, other energy sources, including light, heat, or RF are employed.

SMP foams comprise at least one hard segment and one soft segment. One segment contains a crosslinkable group; linking occurs via charge transfer, chemical or physical segment interactions. Objects formed at a temperature above a $T_{trans}$ of the hard segment and cooled to a temperature below the $T_{trans}$ of the soft segment can return to their original shape with heating above the $T_{trans}$ of the soft segment again. The foams may also incorporate biodegradable materials, such as polyhydroxy acids, polyanhydrides, polyesters, and polyorthoesters, wherein biodegradable linkages preferably comprise ester, amide, anhdride, carbonate, and/or orthoester linkages. Poly(caprolactone), poly(lactide), poly(glycolide), poly(dioxane), or amino acid based isocyanate materials are a few examples of biodegradable polymers. Naturally occurring materials, such as alginates, cellulose, poly(β-hydroxybutyrate), and dextran may also be incorporated.

Figure 4:
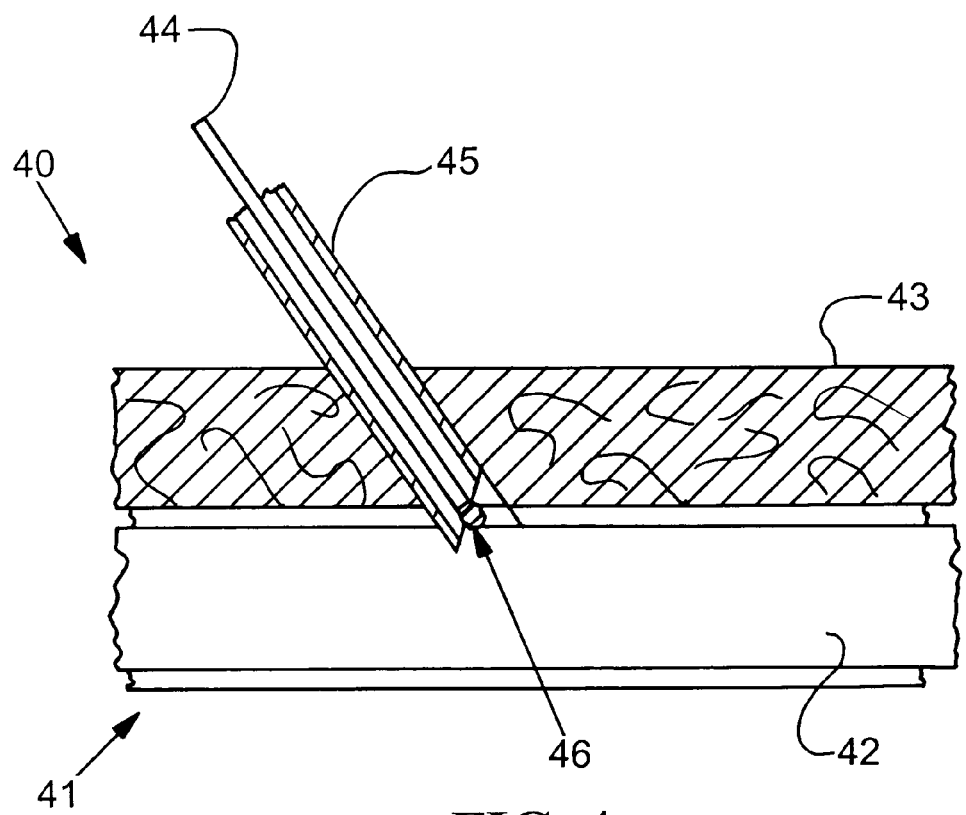
FIG. 4 is a schematic of a puncture tract with a delivery catheter and a SMP foam closure body in its compressed state being moved into place to close a vessel.

FIG. 4 is the fourth of the series of figures that describe an embodiment of the present invention that provides a closure system for procedures such as arteriotomies, septal defect repair or patant foramen ductus closure. FIG. 4 is a schematic of a puncture tract 45 with a delivery catheter 44 and SMP foam closure body 46 in its compressed state being moved into place to close a vessel 41. FIG. 4 is a side section of the puncture tract 45 through the wall of the vessel 41. The puncture tract 45 extends throught the epidermis, dermis, fat 43 into the region of blood flow 42. The illustration of FIG. 4 is designated generally by the reference numeral 40. The schematic 40 illustrates a puncture tract 45 with a delivery catheter 44 for deploying an closure body 46 in its compressed state to the desired location. The delivery catheter comprises an actuation method to deploy the closure body 46 and allows it to reach its expanded (actuated) state. The delivery catheter is then removed from the puncture tract, leaving the closure body behind in the puncture tract.

Figure 5A:
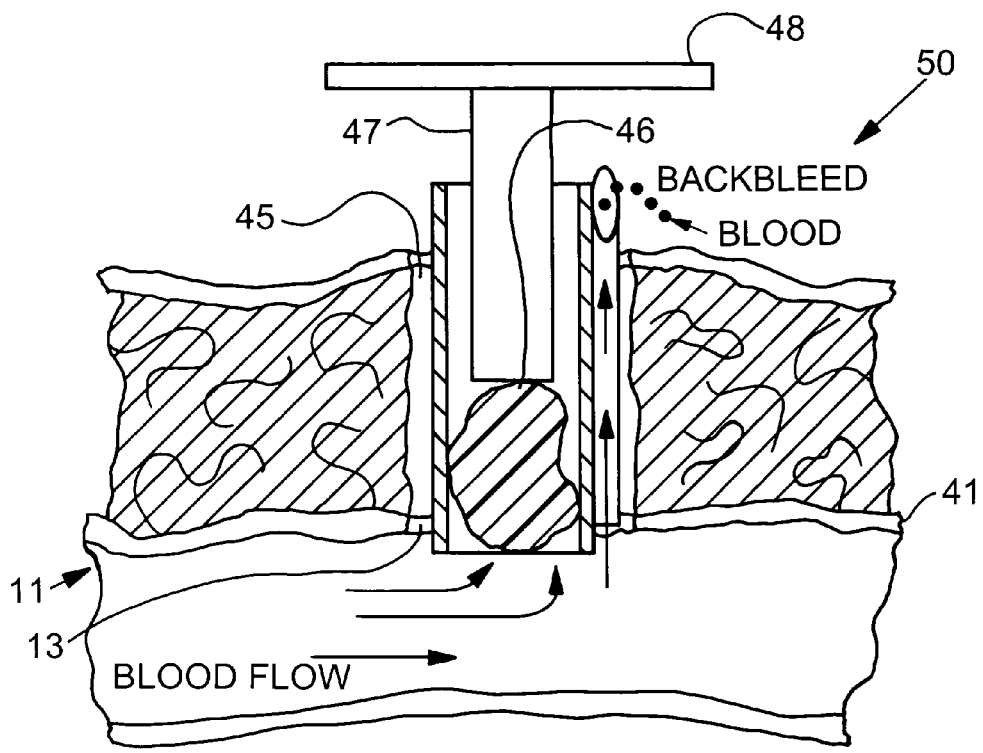
FIGS. 5A, 5B and 5C show a puncture tract 4 with the delivery catheter removed and with the closure body located in position.
Figure 5B:
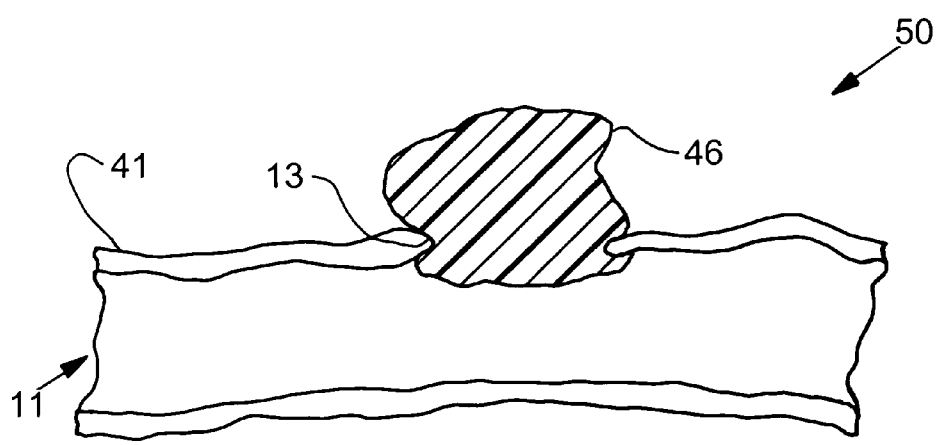
Figure 5C:
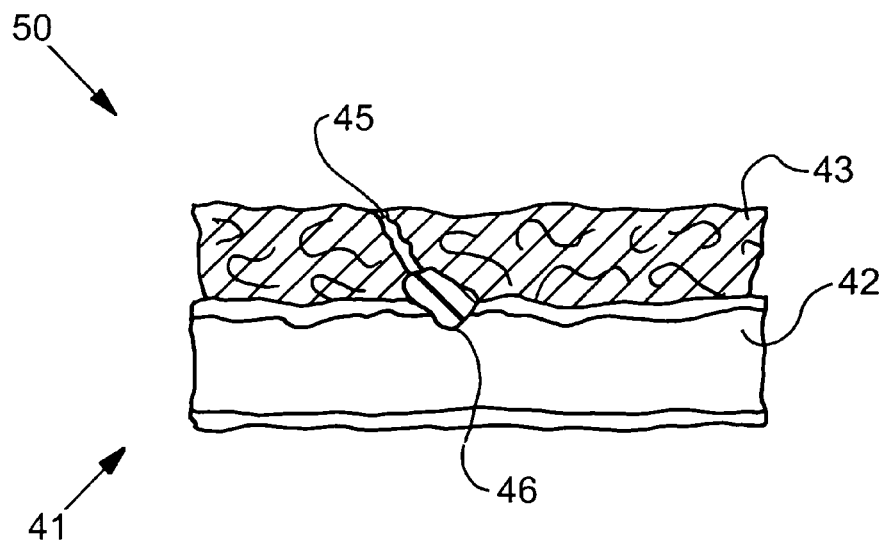

FIGS. 5A, 5B, and 5C are three views that show the fifth of the series of figures that describe embodiments of the present invention that provides a closure system for procedures such as arteriotomies. This embodiment is designated generally by the reference numeral 50 in the three views.

FIG. 5A shows the closure body within the puncture tract prior to expansion 46. A restraint tube 47 and a plunger 48 deploy the closure body into the vessel wall puncture site 13. The restraint tube may allow for backbleed measurement or other physiological measurement, as well as for sensing, for example, via an external tube, a plunger lumen (not shown) or a restraint tube annulus (not shown). The plunger 48 is activated by pulling back on the restraint tube. Full deployment of the SMP foam closure device is shown in FIG. 5B. The closure body 46 is shown in its expanded state (as opposed to compressed state) to fill the gap in the vessel wall in its entirety. In FIG. 5B, the puncture tract 45 is shown with the delivery catheter removed and with the closure body 46 in its expanded (actuated) state.

The closure body 46 in one embodiment is a polymer foam. Polymer blocks used to synthesize foams may be comprised of such materials as poly(vinyl alcohol), polyamides, polycarbonates, polyacrylates, polyacrylamides, and poly(ethylene glycols). Nonbiodegradable materials preferably do not include aromatic groups, with the exception of those derived from natural amino acids. In one embodiment the polymer is a shape memory polymer (SMP).

SMP foams may be soft, rigid, or semi-rigid and their processing may include surfactants, blowing agents and/or fillers, such as chemical porogens. These materials may help control the bubble size, affecting the final pore size, via control of surface energy. Materials may be miscible or immiscible. The foams may be open cell or closed cell, although open cell foams are preferred for cellular ingrowth since they have interconnecting pores. Blowing agents, such as carbon dioxide are preferred over materials such as chlorofluorocarbons. Lyophilization may be used to create foams from polymers dissolved in solution, for example, PLGA suspended in methylene chloride. Spinning processes may also be incorporated into the foam fabrication.

FIG. 5C is a side section of the puncture tract 45 through the wall of the vessel 41. The puncture tract 45 extends through the epidermis, dermis, fat 43 into the region of blood flow 42.

Figure 6:
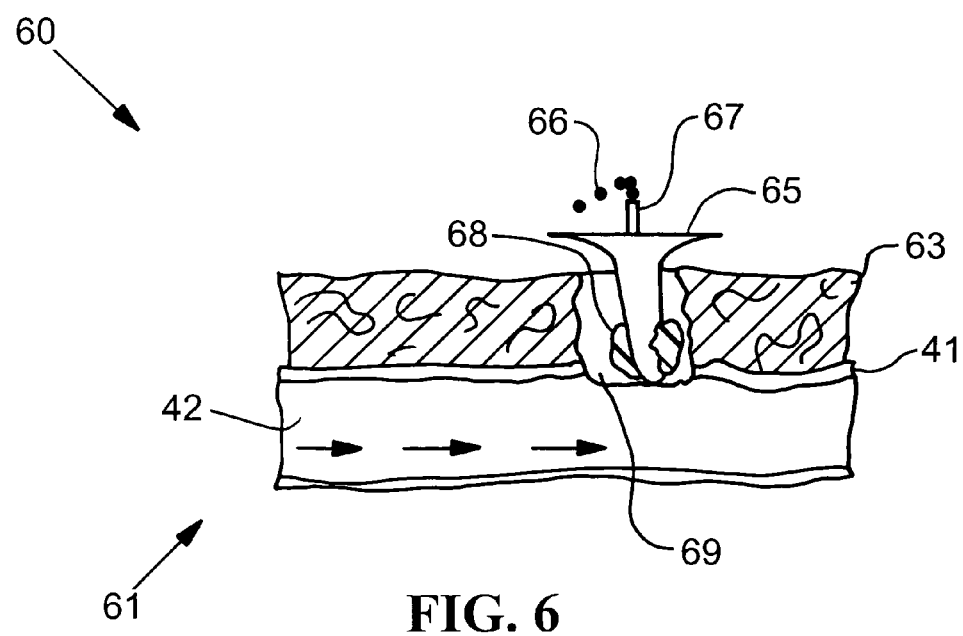
FIG. 6 illustrates another embodiment of the present invention.

Referring now to FIG. 6, another embodiment of the present invention is illustrated. This embodiment is designated generally by the reference numeral 60. A plunger 65 with exemplary SMP foam 68 carried by the plunger 65 is shown positioned in a puncture 69 in a vessel 61 (cross section) through the epidermis, dermis and fat layers, collectively numbered 63. The plunger may comprise a lumen or additional tube 67 to allow for backbleed measurement or other physiological measurement, as well as for sensing. The plunger activates the SMP with light or heat or from externally applied energy.

Figure 7:
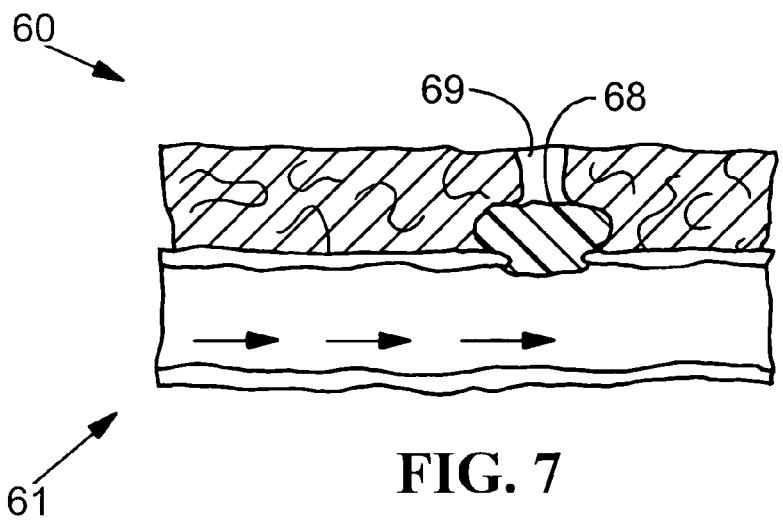
FIG. 7 shows the embodiment of FIG. 6 with full deployment of the SMP foam closure device.

Referring now to FIG. 7, the embodiment 60 is shown with full depolyment of the SMP foam closure device 68. The foam 68 is shown in its expanded state to fill the gap 69 in vessel 61 wall in its entirety. The foam 68 is an SMP, i.e., a polymer which can be formed into a primary or equilibrium shape, re-formed into a stable secondary or stressed shape, and actuated by various means to recover its primary shape. The deployed polymer takes up a larger volume while maintaining a similar shape to the constrained material. SMP foams may be soft, rigid, or semi-rigid and their processing may include surfactants, blowing agents and/or fillers, such as chemical porogens. These materials may help control the bubble size, affecting the final pore size, via control of surface energy. Materials may be miscible or immiscible. The foams may be open cell or closed cell, although open cell foams are preferred for cellular ingrowth since they have interconnecting pores. Blowing agents, such as carbon dioxide are preferred over materials such as chlorofluorocarbons. Lyophilization may be used to create foams from polymers dissolved in solution, for example, PLGA suspended in methylene chloride. Spinning processes may also be incorporated into the foam fabrication.

Figure 8:
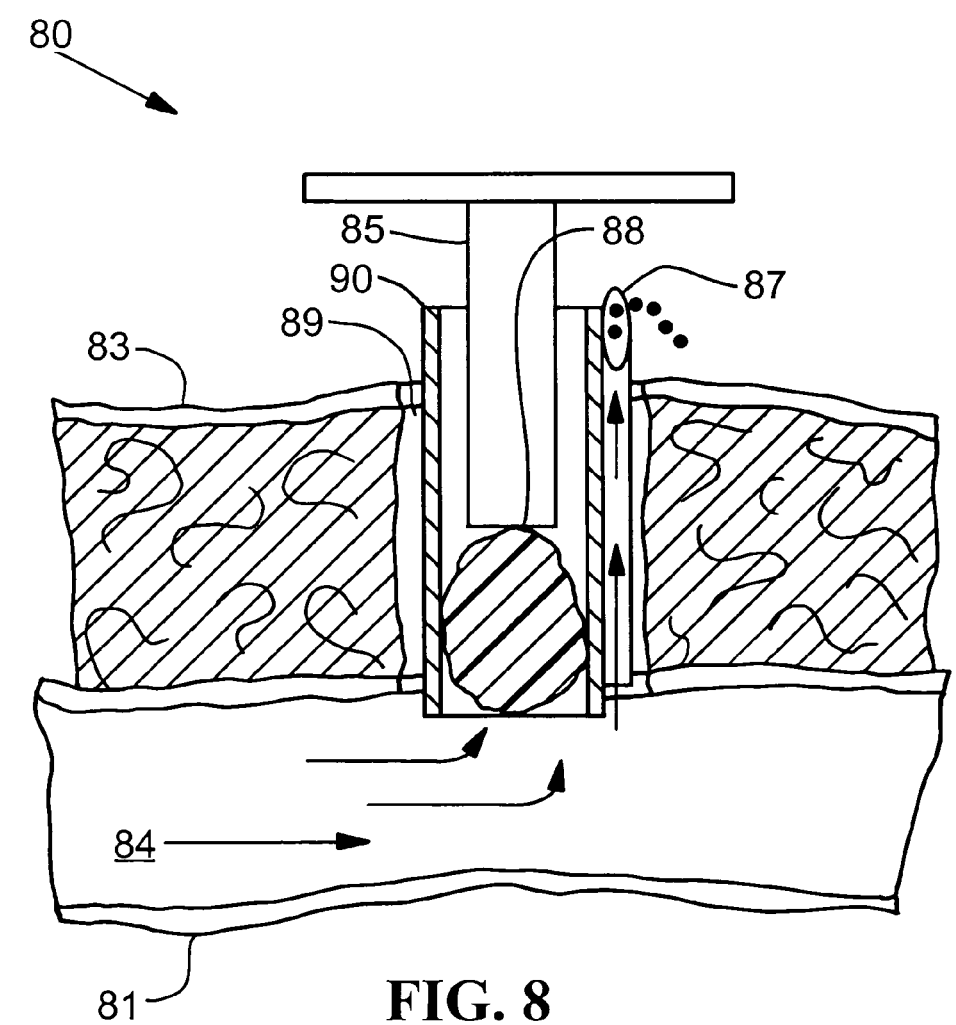
FIG. 8 illustrates another embodiment of the present invention.

Referring now to FIG. 8, another embodiment of the present invention is illustrated. This embodiment is designated generally by the reference numeral 80. A plunger 85 with exemplary SMP foam 88 carried by the plunger 85 is shown positioned in a puncture 89 in a vessel 81 (cross section) and extending through another layer of tissue or the epidermis, dermis, fat 83. The actuator is positioned in a restraint tube 90. A backbleed tube 87 allows for backbleed measurement or other physiological measurement, as well as for sensing. The actuator activates the SMP with light or heat or from externally applied energy, or stress induced, or heated by blood.

Figure 9:
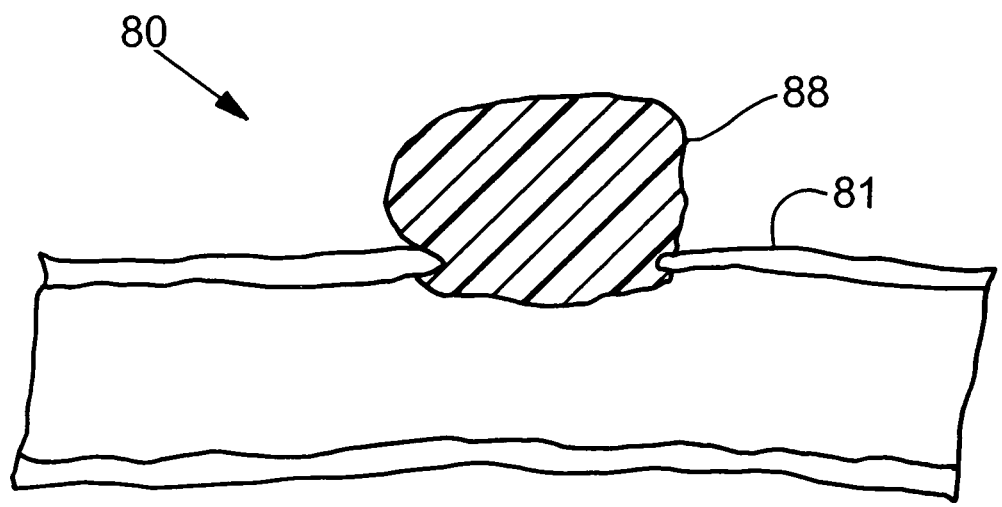
FIG. 9 shows the embodiment of FIG. 8 with full deployment of the SMP foam closure device.

Referring now to FIG. 9, the embodiment 80 is shown with full depoyment of the SMP foam closure device 88. The foam 88 is shown in its expanded state to fill the gap 89 in vessel 81 wall in its entirety. The foam 88 is an SMP, i.e., a polymer which can be formed into a primary or equilibrium shape, re-formed into a stable secondary or stressed shape, and actuated by various means to recover its primary shape. The deployed polymer takes up a larger volume while maintaining a similar shape to the constrained material. SMP foams may be soft, rigid, or semi-rigid and their processing may include surfactants, blowing agents and/or fillers, such as chemical porogens. These materials may help control the bubble size, affecting the final pore size, via control of surface energy. Materials may be miscible or immiscible. The foams may be open cell or closed cell, although open cell foams are preferred for cellular ingrowth since they have interconnecting pores. Blowing agents, such as carbon dioxide are preferred over materials such as chlorofluorocarbons. Lyophilization may be used to create foams from polymers dissolved in solution, for example, PLGA suspended in methylene chloride. Spinning processes may also be incorporated into the foam fabrication.

Figure 10:
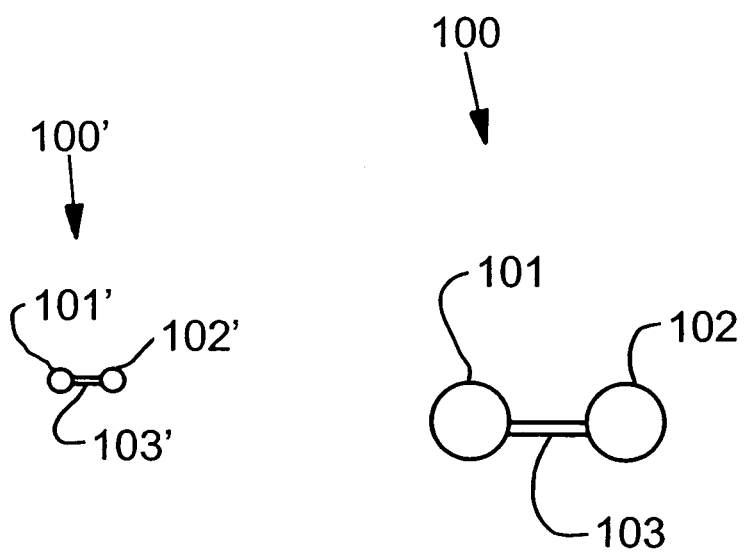
FIG. 10 illustrates an embodiment of a closure body.

Referring now to FIG. 10, one embodiment of a closure body is shown. The embodiment is illustrated in two states and is designated generally by the reference numerals 100 and 100'. The embodiment 100, 100' provides an apparatus for closure of a physical anomaly. The closure is provided by a polymer body with an exterior surface. The exterior surface contacts the opening of the anomaly and closes the anomaly. The polymer body has a secondary shape illustrated by the left figure and designated by the reference numeral 100'. The secondary shape 100' allows polymer closure body to be positioned in the physical anomaly. The primary shape is illustrated by the right figure and is designated by the reference numeral 100. The primary shape 100 allows the polymer closure body's exterior surface to contact inner surface of the passage of the anomaly and closes the anomaly.

Uses of the embodiment 100, 100' include systems for the closure of physical anomalies in general. The embodiment 100, 100' can be used for the closure of punctures in vascular or non-vascular walls in the body. For example, arteriotomy puncture sites result from minimally invasive catheter-based procedures. The embodiment 100, 100' comprises a closure body fabricated from a "shape memory polymer" (SMP), which can be formed into a specific "primary" shape 100, compressed into a "secondary" stable shape 100', then controllably actuated so that it recovers its primary shape 100. The shape of embodiment 100, 100' may be particularly suited for the closure of septal defects or patent ductus.

The embodiment 100, 100' is a "barbell" shape to anchor the polymer body in place effectively. As shown, the primary shape 100 includes two polymer bodies 101 and 102. The two polymer bodies 101 and 102 are connected by an elongated section 103. The secondary shape 100' includes two polymer bodies 101' and 102'. The two polymer bodies 101' and 102' are connected by an elongated section 103'. The polymer bodies 101, 101' and 102, 102' and the connector section 103, 103' in one embodiment are made of a polymer foam. Polymer foams may be soft, rigid, or semi-rigid and their processing may include surfactants, blowing agents and/or fillers, such as chemical porogens. These materials may help control the bubble size, affecting the final pore size, via control of surface energy. Materials may be miscible or immiscible. The foams may be open cell or closed cell, although open cell foams are preferred for cellular ingrowth since they have interconnecting pores. Blowing agents, such as carbon dioxide are preferred over materials such as chlorofluorocarbons. Lyophilization may be used to create foams from polymers dissolved in solution, for example, PLGA suspended in methylene chloride. Spinning processes may also be incorporated into the foam fabrication.

SMP foams comprise at least one hard segment and one soft segment. One segment contains a crosslinkable group; linking occurs via charge transfer, chemical or physical segment interactions. Objects formed at a temperature above a $T_{trans}$ of the hard segment and cooled to a temperature below the $T_{trans}$ of the soft segment can return to their original shape with heating above the $T_{trans}$ of the soft segment again. The foams may also incorporate biodegradable materials, such as polyhydroxy acids, polyanhydrides, polyesters, and polyorthoesters, wherein biodegradable linkages preferably comprise ester, amide, anhdride, carbonate, and/or orthoester linkages. Poly(caprolactone), poly(lactide), poly(glycolide), poly(dioxane), or amino acid based isocyanate materials are a few examples of biodegradable polymers. Naturally occurring materials, such as alginates, cellulose, poly($\beta$-hydroxybutyrate), and dextran may also be incorporated.

Figure 11:
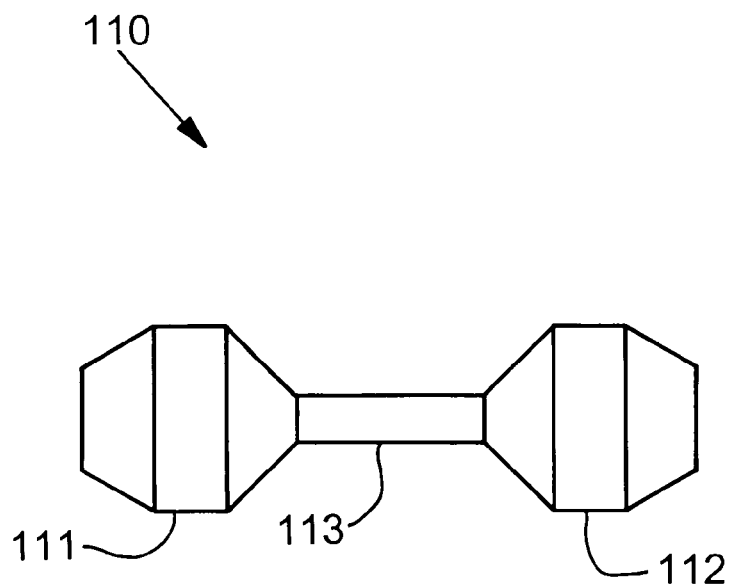
FIG. 11 illustrates another embodiment of a closure body.

Referring now to FIG. 11, another embodiment of a closure body is shown. The embodiment is illustrated in its primary shape and is designated generally by the reference numeral 110. The embodiment 110 provides an apparatus for closure of a physical anomaly. The closure is provided by a polymer body with an exterior surface. The exterior surface contacts the opening of the anomaly and closes the anomaly. The polymer body has a primary shape as illustrated by 110 for closing the anomaly and a secondary shape that is compressed and allows it to be positioned in the physical anomaly.

The embodiment 110 is a "double truncated cone" shape to anchor the polymer body in place effectively. As shown, the primary shape 110 includes two truncated cone polymer bodies 111 and 112. The two truncated cone polymer bodies 111 and 112 are connected by an elongated section 113. The polymer bodies 101 and 102 and the connector section 103 in one embodiment are made of a polymer foam. Polymer foams may be soft, rigid, or semi-rigid and their processing may include surfactants, blowing agents and/or fillers, such as chemical porogens. These materials may help control the bubble size, affecting the final pore size, via control of surface energy. Materials may be miscible or immiscible. The foams may be open cell or closed cell, although open cell foams are preferred for cellular ingrowth since they have interconnecting pores. Blowing agents, such as carbon dioxide are preferred over materials such as chlorofluorocarbons. Lyophilization may be used to create foams from polymers dissolved in solution, for example, PLGA suspended in methylene chloride. Spinning processes may also be incorporated into the foam fabrication.

SMP foams comprise at least one hard segment and one soft segment. One segment contains a crosslinkable group; linking occurs via charge transfer, chemical or physical segment interactions. Objects formed at a temperature above a $T_{trans}$ of the hard segment and cooled to a temperature below the $T_{trans}$ of the soft segment can return to their original shape with heating above the $T_{trans}$ of the soft segment again. The foams may also incorporate biodegradable materials, such as polyhydroxy acids, polyanhydrides, polyesters, and polyorthoesters, wherein biodegradable linkages preferably comprise ester, amide, anhdride, carbonate, and/or orthoester linkages. Poly(caprolactone), poly(lactide), poly(glycolide), poly(dioxane), or amino acid based isocyanate materials are a few examples of biodegradable polymers. Naturally occurring materials, such as alginates, cellulose, poly($\beta$-hydroxybutyrate), and dextran may also be incorporated.

Figure 12:
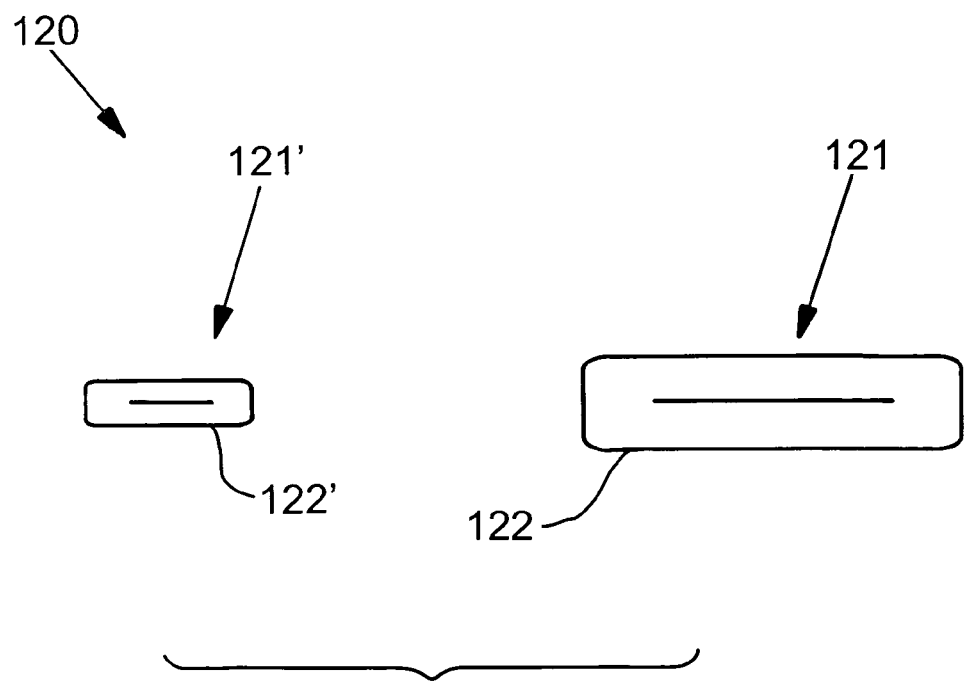
FIG. 12 illustrates an embodiment of a closure body that has a "band" shape.

Referring now to FIG. 12, another embodiment of a closure body is shown. The embodiment 120 is illustrated in two states and is designated generally by the reference numerals 121' and 100'. The embodiment 100, 100' provides an apparatus for closure of a physical anomaly. The closure is provided by a polymer body with an exterior surface. The exterior surface contacts the opening of the anomaly and closes the anomaly. The polymer body has a secondary shape illustrated by the left figure and designated by the reference numeral 121'. The secondary shape 121' allows polymer closure body to be positioned in the physical anomaly. The primary shape is illustrated by the right figure and is designated by the reference numeral 121. The primary shape 121 allows the polymer closure body's exterior surface to contact inner surface of the passage of the anomaly and closes the anomaly. The polymer closure body 121, 121' is a "band" shape with the central opening 122, 122' of the band collapsed.

The embodiment 120 shown in FIG. 12 provides closure of a physical anomaly. The physical anomaly has a passage that needs to be closed. The polymer body 121' has with a secondary shape for being positioned in the passage of the physical anomaly and a primary shape 121 for closing the anomaly. The polymer body 121' is positioned in the passage of the physical anomaly. The polymer body is activated causing the polymer body to change to said primary shape 121 for closing the anomaly.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for closure of a physical anomaly that forms a gap in a vascular wall, the apparatus comprising:
a closure body, said closure body made of a shape memory polymer (SMP) foam,
said shape memory polymer (SMP) foam having at least one hard segment and one soft segment wherein said hard segment is formed at a temperature above $T_{trans}$ and said soft segment is formed at a temperature below $T_{trans}$,
said shape memory polymer (SMP) foam having the ability of being formed into a primary shape at temperature above $T_{trans}$ with a volume larger than the gap in the vascular wall,
said shape memory polymer (SMP) foam having the ability of being compressed into a reduced secondary stable shape by being cooled to a temperature below the $T_{trans}$ with a volume smaller than the gap in the vascular wall,
said shape memory polymer (SMP) foam having the ability of being controllably actuated by being heated to a temperature above the $T_{trans}$ so that it recovers its primary shape with a volume larger than the gap in the vascular wall, and
a delivery device adapted to received said closure body made of a shape memory polymer (SMP) foam with said shape memory polymer (SMP) foam being compressed into said reduced secondary stable shape in said delivery device by being cooled to a temperature below the $T_{trans}$ with a volume smaller than the gap in the vascular wall, said delivery device adapted to deploy said closure body into the physical anomaly in the vascular wall,
wherein said shape memory polymer (SMP) foam of said closure body in said reduced secondary stable shape is configured for positioning said closure body within the physical anomaly in the vascular wall, and
wherein said shape memory polymer (SMP) foam is controllably actuated by being heated to a temperature above the $T_{trans}$ so that it recovers its primary shape with a volume larger than the gap in the vascular wall with said primary shape configured to close said anomaly.

2. The apparatus of claim 1 including actuator means for controllably actuating said shape memory polymer (SMP) foam having at least one hard segment wherein said hard segment is formed at a temperature above $T_{trans}$ by changing said temperature above $T_{trans}$.

3. The apparatus of claim 1 wherein said delivery device includes a tube and a plunger in said tube that deploys said closure body into the physical anomaly in the vascular wall.

4. The apparatus of claim 1 wherein said delivery device includes a tube, a plunger in said tube that deploys said closure body into the physical anomaly in the vascular wall, and a restraint tube for backbleed measurement.

5. The apparatus of claim 1 wherein said delivery device is a delivery catheter.

6. The apparatus of claim 1 wherein said delivery device includes a plunger actuator.

7. The apparatus of claim 1 wherein said delivery device includes a backbleed tube.

8. The apparatus of claim 1 wherein said delivery device includes a plunger actuator and a delivery catheter.

9. The apparatus of claim 1 wherein said delivery device includes a delivery catheter, a plunger actuator, and a restraint tube.

10. The apparatus of claim 1 wherein the physical anomaly is an arteriotomy puncture site.

11. The apparatus of claim 1 including actuator means for controllably actuating said shape memory polymer (SMP) foam, said actuator means configured to transition said closure body from said reduced secondary shape to said primary shape by changing said temperature above $T_{trans}$ by heating.

12. A method of closing a physical anomaly that forms a gap in a vascular wall, the method comprising:
providing a closure body made of a shape memory polymer (SMP) foam,
said shape memory polymer (SMP) foam having at least one hard segment and one soft segment wherein said hard segment is formed at a temperature above $T_{trans}$ and said soft segment is formed at a temperature below $T_{trans}$,
said shape memory polymer (SMP) foam capable of being formed into a primary shape at temperature above $T_{trans}$ with a volume larger than the gap in the vascular wall,
compressing said shape memory polymer (SMP) foam into a reduced secondary stable shape by cooling said shape memory polymer (SMP) foam to a temperature below the $T_{trans}$ with a volume smaller than the gap in the vascular wall,
positioning said closure body made of said shape memory polymer (SMP) foam in the physical anomaly in the vascular wall when said closure body is in said reduced secondary stable shape with a volume smaller than the gap in the vascular wall, and transitioning said closure body made of a shape memory polymer (SMP) foam to said primary shape within the physical anomaly in the vascular wall by heating said shape memory polymer (SMP) foam and changing said temperature above $T_{trans}$ so that it recovers its primary shape with a volume larger than the gap in the vascular wall thereby closing said physical anomaly.

13. The method of claim 12 wherein said step of transitioning the closure body comprises transitioning the closure body with an actuator system that uses light, coherent light, or heat.

14. The method of claim 13, wherein said step of transitioning the closure body comprises transitioning the closure body with an actuator system chosen from the group consisting of external sheaths, removable sheaths, constraint sheaths, light, coherent light, heat, externally applied energy, plungers, RF, induction, stress, and combinations thereof.

15. The method of claim 12 wherein said step of positioning said closure body made of said shape memory polymer (SMP) foam in the physical anomaly in the vascular wall further comprises positioning said closure body made of said shape memory polymer (SMP) foam in the physical anomaly in the vascular wall with a plunger.

16. The method of claim 12 wherein the physical anomaly is chosen from the group consisting of arteriotomy puncture sites, septal defects, patent ductus, and combinations thereof and wherein said step of positioning said closure body made of said shape memory polymer (SMP) foam in the physical anomaly in the vascular wall further comprises positioning said closure body made of said shape memory polymer (SMP) foam in said arteriotomy puncture sites, septal defects, patent ductus, or combinations thereof.

17. A system for the closure of a physical anomaly that forms a gap in a vascular wall, the system comprising:
a closure body for closing the anomaly, said closure body made of a shape memory polymer (SMP) foam,
said shape memory polymer (SMP) foam having at least one hard segment and one soft segment wherein said hard segment is formed at a temperature above $T_{trans}$ and said soft segment is formed at a temperature below $T_{trans}$, said shape memory polymer (SMP) foam having the ability of being formed into a primary shape at temperature above $T_{trans}$ with a volume larger than the gap in the vascular wall, said shape memory polymer (SMP) foam having the ability of being compressed into a reduced secondary stable shape by being cooled to a temperature below the $T_{trans}$ with a volume smaller than the gap in the vascular wall, said shape memory polymer (SMP) foam having the ability of being controllably actuated so that it recovers its primary shape with a volume larger than the gap in the vascular wall, a delivery device adapted to received said closure body made of a shape memory polymer (SMP) foam with said shape memory polymer (SMP) foam being compressed into said reduced secondary stable shape by being cooled to a temperature below the $T_{trans}$ with a volume smaller than the gap in the vascular wall, said delivery device adapted to deploy said closure body into the physical anomaly in the vascular wall, said shape memory polymer (SMP) foam reduced secondary stable shape configured for positioning said closure body in the physical anomaly in the vascular wall, means for positioning said closure body in the physical anomaly in the vascular wall when said closure body is in said reduced secondary stable shape; and means for transitioning said closure body to said primary shape by heating said shape memory polymer (SMP) foam to a temperature above the $T_{trans}$ so that it recovers its primary shape with a volume larger than the gap in the vascular wall for closing said anomaly.

18. The system for the closure of a physical anomaly of claim 17 wherein said shape memory polymer (SMP) foam of said closure body with a secondary shape for being positioned in the physical anomaly and a larger primary shape for closing said anomaly, said shape memory polymer foam having at least one hard segment and one soft segment wherein said hard segment is formed at a temperature above $T_{trans}$ and said soft segment is formed at a temperature below $T_{trans}$ and wherein said means for transitioning said closure body changes said temperature above $T_{trans}$ by heating.

19. The system of claim 17 wherein said means for positioning said closure body in the physical anomaly in the vascular wall is a delivery catheter.

* * * * *